United States Patent
Ramsingh et al.

(10) Patent No.: US 11,780,888 B2
(45) Date of Patent: Oct. 10, 2023

(54) CHIMERIC PROTEIN FOR CORONAVIRUS VACCINE

(71) Applicants: Arlene I. Ramsingh, Miami, FL (US); Janice Pata, Alcove, NY (US)

(72) Inventors: Arlene I. Ramsingh, Miami, FL (US); Janice Pata, Alcove, NY (US)

( * ) Notice: Subject to any disclaimer, the term of this patent is extended or adjusted under 35 U.S.C. 154(b) by 172 days.

(21) Appl. No.: 17/382,625

(22) Filed: Jul. 22, 2021

(65) Prior Publication Data

US 2022/0106363 A1   Apr. 7, 2022

Related U.S. Application Data

(60) Provisional application No. 63/056,377, filed on Jul. 24, 2020.

(51) Int. Cl.
*C07K 14/005* (2006.01)
*A61K 39/215* (2006.01)
*A61K 49/00* (2006.01)

(52) U.S. Cl.
CPC .......... *C07K 14/005* (2013.01); *A61K 39/215* (2013.01); *A61K 49/00* (2013.01); *C12N 2760/16022* (2013.01); *C12N 2760/16034* (2013.01); *C12N 2770/20022* (2013.01); *C12N 2770/20034* (2013.01)

(58) Field of Classification Search
None
See application file for complete search history.

(56) References Cited

FOREIGN PATENT DOCUMENTS

WO   WO-2022020460 A1 *  1/2022

OTHER PUBLICATIONS

Yin L, Zeng Y, Wang W, Wei Y, Xue C, Cao Y. Immunogenicity and protective efficacy of recombinant fusion proteins containing spike protein of infectious bronchitis virus and hemagglutinin of H3N2 influenza virus in chickens. Virus Res. Sep. 2, 2016;223:206-12. doi: 10.1016/j.virusres.2016.07.010. Epub Aug. 3, 2016.*
GenBank Accession QLG99427. Jul. 13, 2020.*
GenBank Accession AGE83723. Feb. 28, 2014.*

* cited by examiner

*Primary Examiner* — Benjamin P Blumel
*Assistant Examiner* — Jeffrey Mark Sifford
(74) *Attorney, Agent, or Firm* — Kathy Smith Dias; Tech Valley Patent, LLC; John Pietrangelo

(57) ABSTRACT

The disclosure relates to a polypeptide comprising, or consisting of, the amino acid sequence of SEQ ID NO: 1, SEQ ID NO: 5, SEQ ID NO: 6, SEQ ID NO: 9 or a sequence having at least 97%-100% sequence identity to one of SEQ ID NO: 1, SEQ ID NO: 5, SEQ ID NO: 6, SEQ ID NO: 9 for use as an immunogen for the purpose of eliciting an immune response in a subject susceptible to infection with a coronavirus. The disclosed polypeptide is further useful in reducing the severity of symptoms associated with a coronavirus infection. In addition to use in a protein-based vaccine, the polypeptide of the disclosure can be encoded by a nucleic acid/ribonucleic acid and used in a nucleic acid vaccine or viral vector vaccine.

6 Claims, No Drawings

Specification includes a Sequence Listing.

SEQUENCE LISTING

```
<160> NUMBER OF SEQ ID NOS: 9

<210> SEQ ID NO 1
<211> LENGTH: 363
<212> TYPE: PRT
<213> ORGANISM: Artificial Sequence
<220> FEATURE:
<223> OTHER INFORMATION: Recombinant polypeptide

<400> SEQUENCE: 1

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Gly Phe Arg His Gln Asn Ser Glu
        195                 200                 205

Gly Thr Gly Gln Ala Ala Asp Leu Lys Ser Thr Gln Ala Ala Ile Asp
    210                 215                 220
```

```
Gln Ile Asn Gly Lys Leu Asn Arg Val Ile Glu Lys Thr Asn Glu Lys
225                 230                 235                 240

Phe His Gln Ile Glu Lys Glu Phe Ser Glu Val Glu Gly Arg Ile Gln
                245                 250                 255

Asp Leu Glu Lys Tyr Val Glu Asp Thr Lys Ile Asp Leu Trp Ser Tyr
            260                 265                 270

Asn Ala Glu Leu Leu Val Ala Leu Glu Asn Gln His Thr Ile Asp Leu
        275                 280                 285

Thr Asp Ser Glu Met Asn Lys Leu Phe Glu Lys Thr Arg Arg Gln Leu
    290                 295                 300

Arg Glu Asn Ala Glu Met Gly Asn Gly Cys Phe Lys Ile Tyr His
305                 310                 315                 320

Lys Cys Asp Asn Ala Cys Ile Glu Ser Ile Arg Asn Gly Thr Tyr Asp
                325                 330                 335

His Asp Val Tyr Arg Asp Glu Ala Leu Asn Asn Arg Phe Gln Ile Lys
            340                 345                 350

Gly Val Glu Leu Lys Ser Gly Tyr Lys Asp Trp
        355                 360

<210> SEQ ID NO 2
<211> LENGTH: 200
<212> TYPE: PRT
<213> ORGANISM: Coronavirus

<400> SEQUENCE: 2

Asn Ile Thr Asn Leu Cys Pro Phe Gly Glu Val Phe Asn Ala Thr Arg
1               5                   10                  15

Phe Ala

<213> ORGANISM: Influenza A

<400> SEQUENCE: 3

Gly Phe Arg His Gln Asn Ser Glu Gly Thr Gly Gln Ala Ala Asp Leu
1               5                   10                  15

Lys Ser Thr Gln Ala Ala Ile Asp Gln Ile Asn Gly Lys Leu Asn Arg
            20                  25                  30

Val Ile Glu Lys Thr Asn Glu Lys Phe His Gln Ile Glu Lys Glu Phe
        35                  40                  45

Ser Glu Val Glu Gly Arg Ile Gln Asp Leu Glu Lys Tyr Val Glu Asp
    50                  55                  60

Thr Lys Ile Asp Leu Trp Ser Tyr Asn Ala Glu Leu Leu Val Ala Leu
65                  70                  75                  80

Glu Asn Gln His Thr Ile Asp Leu Thr Asp Ser Glu Met Asn Lys Leu
                85                  90                  95

Phe Glu Lys Thr Arg Arg Gln Leu Arg Glu Asn Ala Glu Glu Met Gly
            100                 105                 110

Asn Gly Cys Phe Lys Ile Tyr His Lys Cys Asp Asn Ala Cys Ile Glu
        115                 120                 125

Ser Ile Arg Asn Gly Thr Tyr Asp His Asp Val Tyr Arg Asp Glu Ala
    130                 135                 140

Leu Asn Asn Arg Phe Gln Ile Lys Gly Val Glu Leu Lys Ser Gly Tyr
145                 150                 155                 160

Lys Asp Trp

<210> SEQ ID NO 4
<211> LENGTH: 16
<212> TYPE: PRT
<213> ORGANISM: Influenza A

<400> SEQUENCE: 4

Met Lys Thr Ile Ile Ala Leu Ser Tyr Ile Phe Cys Leu Ala Leu Gly
1               5                   10                  15

<210> SEQ ID NO 5
<211> LENGTH: 379
<212> TYPE: PRT
<213> ORGANISM: Artificial sequence
<220> FEATURE:
<223> OTHER INFORMATION: recombinant polypeptide

<400> SEQUENCE: 5

Met Lys Thr Ile Ile Ala Leu Ser Tyr Ile Phe Cys Leu Ala Leu Gly
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp

```
                115                 120                 125
Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
        195                 200                 205

Thr Val Cys Gly Pro Lys Lys Ser Gly Phe Arg His Gln Asn Ser Glu
    210                 215                 220

Gly Thr Gly Gln Ala Ala Asp Leu Lys Ser Thr Gln Ala Ala Ile Asp
225                 230                 235                 240

Gln Ile Asn Gly Lys Leu Asn Arg Val Ile Glu Lys Thr Asn Glu Lys
                245                 250                 255

Phe His Gln Ile Glu Lys Glu Phe Ser Glu Val Glu Gly Arg Ile Gln
            260                 265                 270

Asp Leu Glu Lys Tyr Val Glu Asp Thr Lys Ile Asp Leu Trp Ser Tyr
        275                 280                 285

Asn Ala Glu Leu Leu Val Ala Leu Glu Asn Gln His Thr Ile Asp Leu
    290                 295                 300

Thr Asp Ser Glu Met Asn Lys Leu Phe Glu Lys Thr Arg Arg Gln Leu
305                 310                 315                 320

Arg Glu Asn Ala Glu Glu Met Gly Asn Gly Cys Phe Lys Ile Tyr His
                325                 330                 335

Lys Cys Asp Asn Ala Cys Ile Glu Ser Ile Arg Asn Gly Thr Tyr Asp
            340                 345                 350

His Asp Val Tyr Arg Asp Glu Ala Leu Asn Asn Arg Phe Gln Ile Lys
        355                 360                 365

Gly Val Glu Leu Lys Ser Gly Tyr Lys Asp Trp
    370                 375

<210> SEQ ID NO 6
<211> LENGTH: 415
<212> TYPE: PRT
<213> ORGANISM: Artificial sequence
<220> FEATURE:
<223> OTHER INFORMATION: recombinant polypeptide

<400> SEQUENCE: 6

Met Lys Thr Ile Ile Ala Leu Ser Tyr Ile Phe Cys Leu Ala Leu Gly
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
```

```
                100             105                 110
Asp Asp Phe Thr Gly Cys Val Ile Ala Trp Asn Ser Asn Asn Leu Asp
            115                 120                 125

Ser Lys Val Gly Gly Asn Tyr Asn Tyr Leu Tyr Arg Leu Phe Arg Lys
130             135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
            195                 200                 205

Thr Val Cys Gly Pro Lys Lys Ser Gly Phe Arg His Gln Asn Ser Glu
            210                 215                 220

Gly Thr Gly Gln Ala Ala Asp Leu Lys Ser Thr Gln Ala Ala Ile Asp
225                 230                 235                 240

Gln Ile Asn Gly Lys Leu Asn Arg Val Ile Glu Lys Thr Asn Glu Lys
                245                 250                 255

Phe His Gln Ile Glu Lys Glu Phe Ser Glu Val Glu Gly Arg Ile Gln
                260                 265                 270

Asp Leu Glu Lys Tyr Val Glu Asp Thr Lys Ile Asp Leu Trp Ser Tyr
            275                 280                 285

Asn Ala Glu Leu Leu Val Ala Leu Glu Asn Gln His Thr Ile Asp Leu
            290                 295                 300

Thr Asp Ser Glu Met Asn Lys Leu Phe Glu Lys Thr Arg Arg Gln Leu
305                 310                 315                 320

Arg Glu Asn Ala Glu Glu Met Gly Asn Gly Cys Phe Lys Ile Tyr His
                325                 330                 335

Lys Cys Asp Asn Ala Cys Ile Glu Ser Ile Arg Asn Gly Thr Tyr Asp
                340                 345                 350

His Asp Val Tyr Arg Asp Glu Ala Leu Asn Asn Arg Phe Gln Ile Lys
            355                 360                 365

Gly Val Glu Leu Lys Ser Gly Tyr Lys Asp Trp Ile Leu Trp Ile Ser
            370                 375                 380

Phe Ala Ile Ser Cys Phe Leu Leu Cys Val Val Leu Leu Gly Phe Ile
385                 390                 395                 400

Met Trp Ala Cys Gln Arg Gly Asn Ile Arg Cys Asn Ile Cys Ile
                405                 410                 415

<210> SEQ ID NO 7
<211> LENGTH: 13
<212> TYPE: PRT
<213> ORGANISM: Coronavirus

<400> SEQUENCE: 7

Met Phe Val Phe Leu Val Leu Leu Pro Leu Val Ser Ser
1               5                   10

<210> SEQ ID NO 8
<211> LENGTH: 199
<212> TYPE: PRT
<213> ORGANISM: Influenza A

<400> SEQUENCE: 8

Gly Phe Arg His Gln Asn Ser Glu Gly Thr Gly Gln Ala Ala Asp Leu
```

```
            1               5                   10                  15
Lys Ser Thr Gln Ala Ala Ile Asp Gln Ile Asn Gly Lys Leu Asn Arg
                20                  25                  30

Val Ile Glu Lys Thr Asn Glu Lys Phe His Gln Ile Glu Lys Glu Phe
                35                  40                  45

Ser Glu Val Glu Gly Arg Ile Gln Asp Leu Glu Lys Tyr Val Glu Asp
                50                  55                  60

Thr Lys Ile Asp Leu Trp Ser Tyr Asn Ala Glu Leu Leu Val Ala Leu
65                  70                  75                  80

Glu Asn Gln His Thr Ile Asp Leu Thr Asp Ser Glu Met Asn Lys Leu
                85                  90                  95

Phe Glu Lys Thr Arg Arg Gln Leu Arg Glu Asn Ala Glu Glu Met Gly
                100                 105                 110

Asn Gly Cys Phe Lys Ile Tyr His Lys Cys Asp Asn Ala Cys Ile Glu
                115                 120                 125

Ser Ile Arg Asn Gly Thr Tyr Asp His Asp Val Tyr Arg Asp Glu Ala
                130                 135                 140

Leu Asn Asn Arg Phe Gln Ile Lys Gly Val Glu Leu Lys Ser Gly Tyr
145                 150                 155                 160

Lys Asp Trp Ile Leu Trp Ile Ser Phe Ala Ile Ser Cys Phe Leu Leu
                165                 170                 175

Cys Val Val Leu Leu Gly Phe Ile Met Trp Ala Cys Gln Arg Gly Asn
                180                 185                 190

Ile Arg Cys Asn Ile Cys Ile
                195

<210> SEQ ID NO 9
<211> LENGTH: 412
<212> TYPE: PRT
<213> ORGANISM: Artificial sequence
<220> FEATURE:
<223> OTHER INFORMATION: recombinant polypeptide

<400> SEQUENCE: 9

Met Phe Val Phe Leu Val Leu Leu Pro Leu Val Ser Ser Asn Ile Thr
1               5                   10                  15

Asn Leu Cys Pro Phe Gly Glu Val Phe Asn Ala Thr Arg Phe Ala Ser
                20                  25                  30

Val Tyr Ala Trp Asn Arg Lys Arg Ile Ser Asn Cys Val Ala Asp Tyr
                35                  40                  45

Ser Val Leu Tyr Asn Ser Ala Ser Phe Ser Thr Phe Lys Cys Tyr Gly
                50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
                100                 105                 110

Thr Gly Cys Val Ile Ala Trp Asn Ser Asn Asn Leu Asp Ser Lys Val
                115                 120                 125

Gly Gly Asn Tyr Asn Tyr Leu Tyr Arg Leu Phe Arg Lys Ser Asn Leu
                130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
```

-continued

```
                165                 170                 175
Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
            195                 200                 205

Gly Pro Lys Lys Ser Gly Phe Arg His Gln Asn Ser Glu Gly Thr Gly
    210                 215                 220

Gln Ala Ala Asp Leu Lys Ser Thr Gln Ala Ala Ile Asp Gln Ile Asn
225                 230                 235                 240

Gly Lys Leu Asn Arg Val Ile Glu Lys Thr Asn Glu Lys Phe His Gln
                245                 250                 255

Ile Glu Lys Glu Phe Ser Glu Val Glu Gly Arg Ile Gln Asp Leu Glu
                260                 265                 270

Lys Tyr Val Glu Asp Thr Lys Ile Asp Leu Trp Ser Tyr Asn Ala Glu
            275                 280                 285

Leu Leu Val Ala Leu Glu Asn Gln His Thr Ile Asp Leu Thr Asp Ser
    290                 295                 300

Glu Met Asn Lys Leu Phe Glu Lys Thr Arg Arg Gln Leu Arg Glu Asn
305                 310                 315                 320

Ala Glu Glu Met Gly Asn Gly Cys Phe Lys Ile Tyr His Lys Cys Asp
                325                 330                 335

Asn Ala Cys Ile Glu Ser Ile Arg Asn Gly Thr Tyr Asp His Asp Val
            340                 345                 350

Tyr Arg Asp Glu Ala Leu Asn Asn Arg Phe Gln Ile Lys Gly Val Glu
            355                 360                 365

Leu Lys Ser Gly Tyr Lys Asp Trp Ile Leu Trp Ile Ser Phe Ala Ile
    370                 375                 380

Ser Cys Phe Leu Leu Cys Val Val Leu Leu Gly Phe Ile Met Trp Ala
385                 390                 395                 400

Cys Gln Arg Gly Asn Ile Arg Cys Asn Ile Cys Ile
                405                 410
```

CHIMERIC PROTEIN FOR CORONAVIRUS VACCINE

CROSS-REFERENCE TO RELATED APPLICATIONS

This application claims the priority of U.S. Provisional application No. 63/056,377 filed Jul. 24, 2020, the contents of which are hereby incorporated by reference in their entirety into the instant disclosure.

FIELD OF THE DISCLOSURE

The disclosure relates to an immunogenic polypeptide and compositions for treatment of or protection from infection by coronavirus. In particular, the disclosure relates to a chimeric polypeptide for immunizing subjects against coronavirus, such as SARS CoV-2.

BACKGROUND

The desperate need for a COVID-19 vaccine has given rise to over 160 vaccine candidates that are currently under study around the world. These utilize four main platforms: RNA vaccines, DNA vaccines, recombinant protein vaccines, and vectored vaccines, each of which has specific advantages and disadvantages (reviewed in Corey et al. A strategic approach to COVID-19 vaccine R & D. Science 368:948-950, 2020, which is herein incorporated by reference in its entirety into the instant disclosure).

Nucleic acid vaccines can be generated rapidly once a viral target sequence is identified. However, while there had been a fair amount of data on the use of nucleic acid vaccines in early-phase clinical tests, prior to development and emergency use of covid-2 vaccines by Pfizer/BioNTech and Moderna, none had been approved for widespread use.

Replication-defective adenoviral vectors are generally safe and immunogenic but pre-existing immunity to the vector can hamper immunogenicity.

Recombinant protein vaccines (influenza, papillomavirus, hepatitis B, varicella-zoster) are in widespread use in the human population but require more time to manufacture than nucleic acid vaccines.

The majority of COVID-19 vaccine candidates target the Spike (S) glycoprotein of SARS-CoV-2. The S glycoprotein is a favored target because it is generally accepted that neutralizing antibodies against it play a predominant role in protection from infection. SARS-CoV-2 has, however, developed multiple strategies to evade or by-pass the immune system.

The S glycoprotein has at least two such strategies. First, a dense glycan shield covers the region in the S glycoprotein that makes contact with the cell's receptor for entry (Wrapp et al. 2020). Second, the S protein contains immunodominant sequences that induce antibodies that are not neutralizing (He et al. 2004; 2006). An effective vaccine will have to circumvent the immune evasion strategies of this virus.

To overcome problems with the prior art approaches, the instant disclosure provides an alternative strategy, in particular with respect to designing a suitable immunogen that overcomes the immune avoidance strategies of the virus, and induces a robust and protective immune response.

SUMMARY OF THE DISCLOSURE

In one aspect, the disclosure relates to a recombinant, chimeric, non-naturally occurring polypeptide consisting of or comprising the amino acid sequence of SEQ ID NO: 1 (see Table 1 below) or a sequence having at least 97% sequence identity to SEQ ID NO: 1. The polypeptide comprises a modified Spike receptor-binding domain (RBD) and an HA2 sequence lacking the transmembrane domain. Using methods known to those of skill in the art, the polypeptide can be expressed in a variety of vaccine platforms.

In another aspect, the disclosure relates to a polypeptide comprising consisting of the sequence of SEQ ID NO: 5 (see Table 1) or a sequence having at least 97% sequence identity to SEQ ID NO: 5. The polypeptide comprises the modified S RBD, the HA2 sequence lacking the transmembrane domain plus an HA signal sequence, which enables the polypeptide to be expressed as a secreted molecule.

In yet another aspect, the disclosure relates to a polypeptide comprising or consisting of the sequence of SEQ ID NO: 6 (see Table 1) or a sequence having at least 97% sequence identity to SEQ ID NO: 6. This polypeptide comprises the modified S RBD sequence, an HA signal sequence, the HA2 sequence including the transmembrane domain.

In another aspect, the disclosure relates to a polypeptide comprising or consisting of the sequence of SEQ ID NO: 9 (see Table 1) or a sequence having at least 97% sequence identity to SEQ ID NO: 9. This polypeptide comprises the modified S RBD sequence, an S protein signal sequence, and HA2 sequence including the transmembrane domain.

In another aspect, the disclosure relates to a nucleic acid that encodes a polypeptide of SEQ ID NO: 1, SEQ ID NO: 5, SEQ ID NO: 6, or SEQ ID NO: 9 or an amino acid sequence having at least 97% sequence identity to one of SEQ ID NOS: 1, 5, 6, or 9.

In yet another aspect, the disclosure relates to a composition comprising an amino acid with the amino acid sequence of SEQ ID NO: 1, SEQ ID NO: 5, SEQ ID NO: 6, or SEQ ID NO: 9 or an amino acid sequence having at least 97% sequence identity to one of SEQ ID NOS: 1, 5, 6, or 9.

In yet another aspect, the disclosure relates to a vector comprising a nucleic acid that encodes an amino acid sequence of SEQ ID NO: 1, SEQ ID NO: 5, SEQ ID NO: 6, or SEQ ID NO: 9 or an amino acid sequence having at least 97% sequence identity to one of SEQ ID NOS: 1, 5, 6, or 9.

In one aspect, the disclosure relates to a composition comprising a viral vector, said viral vector comprising a nucleic acid encoding a polypeptide of SEQ ID NO: 1, SEQ ID NO: 5, SEQ ID NO: 6, or SEQ ID NO: 9 or an amino acid sequence having at least 95% sequence identity to one of SEQ ID NOS: 1, 5, 6, or 9.

In one aspect, the invention relates to a composition as described above, wherein said composition is a pharmaceutical composition.

In one aspect, the invention relates to a composition as described above, wherein said composition is a vaccine composition.

In one aspect, the invention relates to a composition as described above, wherein said composition is capable of inducing a protective immune response against SARS-Cov-2 in a human.

TABLE 1

| SEQ ID NO: | | Description |
|---|---|---|
| 1 | NITNLCPFGE VFNATRFASV | An embodiment of the polypeptide of the |

TABLE 1-continued

| SEQ ID NO: | | Description |
|---|---|---|
| | YAWNRKRISN CVADYSVLYN SASFSTFKCY GVSPTKLNDL CFTNVYADSF VIRGDEVRQI APGQTGKIAD YNYKLPDDFT GCVIAWNSNN LDSKVGGNYN YLYRLFRKSN LKPFERDIST EIYQAGSTPC NGVEGFNCYF PLQSYGFQPT NGVGYQPYRW VLSFELLHAP ATVCGPKKSG FRHQNSEGTG QAADLKSTQA AIDQINGKLN RVIEKTNEKF HQIEKEFSEV EGRIQDLEKY VEDTKIDLWS YNAELLVALE NQHTIDLTDS EMNKLFEKTR RQLRENAEEM GNGCFKIYHK CDNACIESIR NGTYDHDVYR DEALNNRFQI KGVELKSGYK DW | disclosure comprising modified Spike RBD and HA2 (without transmembrane domain of HA2) |
| 2 | NITNLGPFGE VFNATRFASV YAWNRKRISM CVADYSVLYN SASFSTFKCY GVSPTKLNDL CFTNWADSFV IRGDEVRQIA PGQTGKIADY NYKLPDDFTG CVIAWNSNNL DSKVGGNYNY LYRLFRKSNL KPFERDISTE IYQAGSTPCN GVEGFNCYFP LQSYGFQPTM GVGYQPYRWV LSFELUHAPA TVCGPKKS | Spike (S) RBD |
| 3 | GFRHQNSEGT GQAADLKSTG AAIDQINGKL NRVIEKTNEK FHQIEKEFSE VEGRIQDLEK YVEDTKIDLW SYNAELLVAL ENQHTIDLTD SEMNKLFEKT RRQLRENAEE MGNGCFKIYH KCDNACIESI RNGTYDHDVY RDEALNNRFQ IKGVELKSGY KDW | HA2 minus transmembrane domain residues 23-185 |
| 4 | MKTIIALSYI FCLALG | HA signal sequence |
| 5 | MKTIIALSYI FCLALGNITN LCPFGEVF NATRFASVYA WNRKRISNCV ADYSVLYMSA SFSTFKCYGV SPTKLNDLCF TNVYADSFVI RGDEVRQIAP GQTGKIADYN YKLPDDFTGC VIAWNSNNLD SKVGGNYNYL YRLFRKSNLK PFERDISTEI YQAGSTPCNG VEGFNGYFPL QSYGFQPTKG VGYQPYRWVL SFELLHAPAT VCGPKKSGFR HQNSEGTGQA ADLKSTQAAD QINGKLNRVI EKTNEKFHQI EKEFSEVEGR IQDLEKWEDT KIDLWSYNAE LLVALENGHT IDLTDSEMNK LFEKTRRQLR ENAEEMGNGC FKIYHKCDNA CIESIRNGTY DHDVYRDEAL NNRFQIKGVE LKSGYKDW | Embodiment of polypeptide to be expressed as secreted molecule |
| 6 | MKTIIALSYI FCLALGNITN LCPFGEVFNA TRFASWAWNR KRISNCVADY SVLYNSASFS TFKCYGVSPT KLNQLCFTNV YADSFVIRGD EVRQIAPGQT GKIADYNYKL PDDFTGCVIA WNSNNLDSKV GGNYNYLYRL FRKQNLKPFE RDISTEIYQA GSTPCNGVEG FNCYFPIQSY GFQPTNGVGY QPYRWVLSFE LLHAPATVCG PKKSGFRHQN SEGTGQMDLK STQAAIDQIN GKLNIRVIEK TNEKFHQIEK EFSEVEGRIQ DLEKYVEDTK IDLWSYNAEL LVALENQHTI DLTDSEMNKL FEKTRRQLRE NAEEMGNGCF | Embodiment of polypeptide to be expressed as plasma membrane-bound molecule |

TABLE 1-continued

| SEQ ID NO: | | Description |
|---|---|---|
| | KIYHKCDNAC IESIRNGTYD HDVYRDEALN NRFQIKGVEL KSGYKDWILW ISFAISCFLL CWLLGFIMWA CQRGNIRCNI CI | |
| 7 | MFVFLVLLPL VSS | Spike signal sequence |
| 8 | GFRHQNSEGT GQAADLKSTQ AAIDQFNGKL NRVIEKTNEK FHQIEKEFSE VEGRIQDLEK YVEDTKIDLW SYNAELLVAL ENQHTIDLTD SEMNKLFEKT RRQLRENAEE MGNGCFKIYH KCDNACIESI RNGTYDHDVY RDEALNNRFQ IKGVELKSGY KDWILWISFA ISCFLLCWLL GFIMWACQRG NIRCNICI | HA2 sequence including transmembrane sequence |
| 9 | MFVFLVUPLV SSNITNLCPF GEVFNATRFA SVYAWNRKRI SNCVADYSVL YNSASFSTFK CYGVSPTKLN DLCFTNVYAD SFVIRGDEVR QFAPGQTGKI ADYNYKLPDD FTGCVIAWNS NNLDSKVGGN YNYLYRLFRK SNLKPFERDI STEIYQAGST PCNGVEGFNC YFPLQSYGFQ PTNGVGYQPY RWVLSFELLH APATVCGPKK SGFRHQNSEG TGQAADLKST QAAIDQINGK LNRVIEKTNE KFHQIEKEFS EVEGRIQDLE KYVEDTKIDL WSYNAELLVA LENQHTIDLT DSEMNKLFEK TRRQLRENAE EMGNGCFKIY HKCDNACIES IRNGTYDHDV YRDEALNNRF QIKGVELKSG YKDWILWISF AISCFLLCWL LGFIMWACQR GNIRCNICI | Polypeptide to be expressed as an ER/Golgi membrane-bound molecule comprising Covid-19 S protein signal sequence, RBD and HA2 including transmembrane sequence |

DETAILED DESCRIPTION

All patents, published applications and other publications and references are hereby incorporated by reference in their entirety into the present disclosure.

As discussed above, the majority of COVID-19 vaccine candidates target the S glycoprotein of SARS-CoV-2 because it is generally accepted that neutralizing antibodies against it play a predominant role in protection from infection. SARS-CoV-2 has, however, developed multiple strategies to evade or by-pass the immune system.

The S glycoprotein has at least two such strategies. First, a dense glycan shield covers the region in the S glycoprotein that makes contact with the cell's receptor for entry (Wrapp et al. Cryo-EM Structure of the 2019-nCoV Spike in the Prefusion Conformation. Science 367: 1260-1263, 2020, which is hereby incorporated by reference in its entirety into the instant disclosure).

Second, the S protein contains immunodominant sequences that induce antibodies that are not neutralizing (He et al. Identification of Immunodominant Sites on the Spike Protein of Severe Acute Respiratory Syndrome (SARS) Coronavirus: implication for Developing SARS Diagnostics and Vaccines. J. Immunol. 173:4050-4057, 2004; and He et al. Antigenic and immunogenic Characterization of Recombinant Baculovirus-Expressed Severe Acute Respiratory Syndrome Coronavirus Spike Protein: Implication for Vaccine Design. J. Virol. 80(12): 5757-5767, 2006; both are hereby incorporated by reference in their entirety into the instant disclosure). An effective vaccine will have to circumvent the immune evasion strategies of this virus.

The present disclosure describes a recombinant polypeptide useful for eliciting an immune response in a subject who is susceptible to infection with coronavirus. The polypeptide is a chimera comprising elements of the S protein of SARS-Cov-2 as well as a hemagglutinin (HA) moiety of influenza virus, a chimera, which can be expressed in any of four known vaccine platforms.

In designing a new vaccine candidate, three main hurdles were addressed: (1) the inherent immune evasion strategies of the S glycoprotein, (2) the necessity of manufacturing hundreds of millions of vaccine doses, and (3) protection from future coronavirus pandemics. The vaccine candidate of the disclosure is a chimeric molecule that overcomes these obstacles.

Immunogen Design

To counter the two immune evasion strategies of the native S glycoprotein, the vaccine target had to be modified. This was done by removing the amino-terminal sequence of Spike, which is heavily glycosylated, along with the carboxy-terminal sequence that induces non-neutralizing antibodies. The resulting vaccine target is a modified RBD (receptor-binding domain) containing multiple neutralization antigenic sites and just two glycosylation sites. (RBD portion of Spike glycoprotein of Covid-19: Genbank: QHU79173.2 surface glycoprotein [Severe acute respiratory syndrome coronavirus 2])

The next step involved choosing a protein stalk for the modified RBD that is capable of trimerization since trimers are generally more immunogenic than monomers. The protein stalk was also chosen with scale-up in mind. The HA2 moiety of influenza virus (HA2 of influenza A can be found at the following url: uniprot.org/uniprot/P03437:>sp|P03437|HEMA_I68A0 Hemagglutinin OS=Influenza A virus (strain A/Aichi/2/1968 H3N2) OX=387139 GN=HA PE=1 SV=1) was chosen as the stalk because HA2 is also immunologically quiescent, allowing for focusing of the immune response to the neutralization antigenic sites in the RBD. In one embodiment, the resulting chimeric protein consists of the RBD of SARS-CoV-2 tethered to the HA2 moiety of influenza virus. Importantly, since about half of the chimeric protein is hemagglutinin, scale-up for a protein vaccine could utilize existing technologies that produce massive doses of flu vaccines comprising the hemagglutinin molecule (Flublok, Flucelvax).

In one embodiment, the chimeric protein molecule was subsequently refined using a molecular modeling approach. Recent work by Wrapp et al. (Cryo-EM Structure of the 2019-nCoV Spike in the Prefusion Conformation. Science 367: 1260-1263, 2020) resolved the structure of the S trimer in its pre-fusion state. The predominant state of the trimer has one of the three RBDs rotated up which allows the display of neutralization sensitive epitopes. The chimeric molecule described herein retains the pre-fusion state of RBD for display of epitopes and the post-fusion state of HA2 for trimeric structure.

An initial study to evaluate the immunogenicity of the disclosed polypeptide on a self-amplifying RNA vaccine platform was performed. Mice were immunized intramuscularly with the RNA vaccine version of the disclosed polypeptide and blood samples were collected two weeks later. Serum samples were assayed by ELISA for RBD-specific IgG antibodies. Mice immunized with the chimeric protein vaccine induced a robust RBD-specific Ab response (data not shown.)

Four weeks after immunization, serum samples were assayed for neutralization activity against SARS-CoV-2 using a plaque reduction assay. The chimeric protein vaccine induced a strong neutralizing antibody response.

Lastly, the design of the disclosed chimeric protein lends itself to a pan-coronavirus vaccine strategy. For example, the RBD sequence of SARS-CoV-2 could easily be swapped out of the polypeptide of the disclosure and replaced with that of other coronaviruses, SARS-CoV-3, -4, -5 etc., to generate vaccines for subsequent pandemics.

The invention claimed is:

1. A recombinant polypeptide consisting of the amino acid sequence of SEQ ID NO: 1.
2. An isolated nucleic acid that encodes the recombinant polypeptide of claim 1.
3. The isolated nucleic acid of claim 2, wherein the isolated nucleic acid is DNA.
4. The isolated nucleic acid of claim 2, wherein the isolated nucleic acid is RNA.
5. A composition comprising the recombinant polypeptide of claim 1 and a pharmaceutically acceptable carrier.
6. A method of reducing the likelihood of infection of a subject with a coronavirus comprising administering to said subject a therapeutically effective amount of a composition of claim 5.

* * * * *